US009024223B2

(12) United States Patent
Miyamoto et al.

(10) Patent No.: US 9,024,223 B2
(45) Date of Patent: May 5, 2015

(54) OPTICAL TYPE GRANULE SORTING MACHINE

(71) Applicant: Satake Corporation, Tokyo (JP)

(72) Inventors: Tomoyuki Miyamoto, Hiroshima (JP); Hideaki Ishizu, Hiroshima (JP); Yoshikazu Tateishi, Hiroshima (JP); Masazumi Hara, Hiroshima (JP)

(73) Assignee: Satake Corporation, Tokyo (JP)

( * ) Notice: Subject to any disclaimer, the term of this patent is extended or adjusted under 35 U.S.C. 154(b) by 0 days.

(21) Appl. No.: 14/387,545

(22) PCT Filed: Feb. 7, 2013

(86) PCT No.: PCT/JP2013/052838
§ 371 (c)(1),
(2) Date: Sep. 24, 2014

(87) PCT Pub. No.: WO2013/145873
PCT Pub. Date: Oct. 3, 2013

(65) Prior Publication Data
US 2015/0076042 A1 Mar. 19, 2015

(30) Foreign Application Priority Data

Mar. 27, 2012 (JP) ................................. 2012-070766

(51) Int. Cl.
*B07C 5/342* (2006.01)
*G01J 3/46* (2006.01)
(Continued)

(52) U.S. Cl.
CPC ............... *B07C 5/3425* (2013.01); *G01J 3/465* (2013.01); *G01J 3/50* (2013.01); *G01N 21/85* (2013.01);
(Continued)

(58) Field of Classification Search
CPC ...... B07C 5/3425; B07C 5/342; B07C 5/366; B07C 5/3422; B07C 5/365
USPC ......... 209/580, 581, 587, 638, 639, 644, 932, 209/938
See application file for complete search history.

(56) References Cited

U.S. PATENT DOCUMENTS

| | | |
|---|---|---|
| 2004/0131251 A1 | 7/2004 | Sasaki |
| 2009/0097746 A1 | 4/2009 | Shinjo et al. |
| 2010/0315435 A1 | 12/2010 | Ishida et al. |

FOREIGN PATENT DOCUMENTS

| | | |
|---|---|---|
| JP | 2001-283153 A | 10/2001 |
| JP | 2004-283153 A | 6/2004 |

(Continued)

*Primary Examiner* — Jeffrey Shapiro
(74) *Attorney, Agent, or Firm* — Joseph P. Farrar, Esq.

(57) ABSTRACT

An optical type granule sorting machine is provided which allows a sensitivity setting to be easily performed by effectively utilizing RGB three-dimensional color space information similar to information obtained via human eyes and which enables signal processing to be substantially simplified. Determination means includes a three-dimensional color distribution data creation section that creates data on wavelength components of R light, G light, and B light from the granules, on a three-dimensional color space, a Mahalanobis distance interface creation section that sets an interface calculated based on a Mahalanobis distance to partition the data into a conforming-granule cluster area and a nonconforming granule cluster area, a Euclidean distance interface creation section that determines a position of center of gravity of the conforming granule cluster area and a position of center of gravity of the nonconforming granule cluster area to set an interface calculated based on a Euclidean distance at which the positions of center of gravity lie at a longest distance from each other, and a threshold determination section that determines a line of intersection between the interface calculated based on the Mahalanobis distance and the interface calculated based on the Euclidean distance, to determine the line of intersection to be a determination threshold that allows determination of whether or not the granules are to be treated as a separation target.

2 Claims, 7 Drawing Sheets

(51) Int. Cl.
- *G01J 3/50* (2006.01)
- *G01N 21/85* (2006.01)
- *G01N 21/27* (2006.01)
- *H04N 1/60* (2006.01)
- *G06T 11/00* (2006.01)
- *H04N 9/04* (2006.01)
- *G06T 7/40* (2006.01)

(52) U.S. Cl.
CPC ........ *G01N 21/27* (2013.01); *G01N 2021/8592* (2013.01); *H04N 1/6058* (2013.01); *G06T 11/001* (2013.01); *H04N 9/045* (2013.01); *G06T 7/408* (2013.01); *G06T 2207/10024* (2013.01); *Y10S 209/932* (2013.01); *Y10S 209/938* (2013.01)

(56) References Cited

FOREIGN PATENT DOCUMENTS

| | | |
|---|---|---|
| JP | 2005-186053 A | 7/2005 |
| JP | 2007-006142 A | 1/2007 |
| JP | 2009-119410 A | 6/2009 |
| JP | 2010-050832 A | 3/2010 |
| JP | 2010-062929 A | 3/2010 |
| JP | 2010-288163 A | 12/2010 |
| WO | WO-2008/001889 A1 | 1/2008 |

OPTICAL TYPE GRANULE SORTING MACHINE

TECHNICAL FIELD

The present invention relates to an optical type granule sorting machine which sorts granules such as grains such as rice or wheat or resin pellets into conforming granules and nonconforming granules and which removes foreign substances mixed in the granules by blowing air against the granules.

BACKGROUND ART

Conventionally, an optical determination apparatus has been provided which includes, in order to improve the accuracy of determination of whether or not granules are conforming or nonconforming, transfer means for transferring a material, optical detection means with a light source section that irradiates the material transferred by the transfer means with light with a plurality of wavelengths and an image pickup section that picks up an image of reflected light and/or transmitted light from the material, and determination means for determining the material by comparing density values at two wavelengths in image pickup data taken by the optical detection means with threshold areas of predetermined density values at the two wavelengths (Patent Literature 1). In the optical determination apparatus, when the determination means sets the threshold areas, the image pickup section picks up an image of reflected light and/or transmitted light from a material sample to be determined which has been transferred by the transfer means, the determination means draws density values at any two wavelengths in the image pickup data, on a two-dimensional graph, determines, for all pixels with the respective density values drawn on the two-dimensional graph, whether or not a circle between two points with a diameter defined by those of the pixels which are located at two different points contains any pixel other than the pixels at the two points, joins the pixels at the two points with a connection line only when the determination indicates that the circle between two points contains no pixel other than the pixels at the two points, and sets a closed area drawn by joining such connection lines together to be the threshold area.

In the optical determination apparatus disclosed in Patent Literature 1, the outer shapes of the threshold areas set by the determination means are accurately defined so as not to include a determination area. The optical determination apparatus is thus advantageously effective in that the threshold areas allow the material to be determined and in that sorting based on the determination is also accurate.

However, to simplify an enormous amount of complicated information (a CCD camera serving as the image pickup section in Patent Literature 1 enables, for each of colors, red, green, and blue, 256 types of hues to be distinguished from one another for 8 bits, thus allowing a total of as many as 16,777, 216 types of colors to be distinguished from one another for three-dimensional RGB color space information), the optical determination apparatus disclosed in Patent Literature 1 plots the density value for each of the colors, red, green, and blue acquired by the CCD camera on each of two-dimensional graphs including a red (X axis)-green (Y axis) two-dimensional graph, a green (X axis)-blue (Y axis) two-dimensional graph, and a red (X axis)-blue (Y axis) two-dimensional graph to acquire three-dimensional RGB color space information based on the three two-dimensional graphs.

Acquiring three-dimensional RGB color space information based on the two-dimensional graphs is advantageous when a signal algorithm is very simple and an enormous amount of complicated information is handled. However, since information on two-dimensional planes is observed based on the two-dimensional graphs, a sensitivity setting is disadvantageously limited. Furthermore, not all pieces of RGB color space information can be simultaneously handled, and thus, the above-described optical determination apparatus is disadvantageously not efficient.

CITATION LIST

Patent Literature

Patent Literature 1 Japanese Patent Laid-Open No. 2009-119410

SUMMARY OF INVENTION

Technical Problem

With the foregoing in view, it is a technical object of the present invention to provide an optical type granule sorting machine that allows a sensitivity setting to be easily performed by effectively utilizing RGB three-dimensional color space information similar to information obtained via human eyes and which enables signal processing to be substantially simplified.

Solution to Problem

To accomplish the object, the present invention takes technical measures by providing an optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on individual color information on the granules inspected by the inspection means, and exclusion means for excluding the separation target determined by the determination means from the continuous flow, wherein the inspection means includes an illumination section that illuminates the granules with light and an optical detection section that detects light transmitted through the granules or reflected from the granules, and the determination means includes a three-dimensional color distribution data creation section that plots wavelength components of R light, G light, and B light from the granules detected by the optical detection section on a three-dimensional color space to create three-dimensional color distribution data for a granule sample, a Mahalanobis distance interface creation section that sets an interface calculated based on a Mahalanobis distance in the three-dimensional color distribution data created by the three-dimensional distribution data creation section to partition the data into a first conforming granule cluster area containing many conforming granules and a first nonconforming granule cluster area containing many nonconforming granules and foreign substances, a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area and a second nonconforming granule cluster area, and a threshold determination section that determines a line of intersection between the interface calculated based on the Mahalanobis distance and the interface calculated based on the Euclidean distance, to determine the line of intersection to be a determination threshold that allows determination of whether or not the granules are to be treated as a separation target.

Thus, in the determination means, the three-dimensional color distribution data creation section plots the wavelength components of the R light, G light, and B light of the granules on the three-dimensional color space and considers the entire three-dimensional color distribution of the granule sample to be one cluster area. Then, the Mahalanobis distance interface creation section sets an interface calculated based on the Mahalanobis distance all over the three-dimensional color distribution to divide the data into approximately two clusters, the first conforming granule cluster area mostly containing a granule sample and the first nonconforming granule cluster area mostly containing nonconforming granules and foreign substances. Moreover, the Euclidean distance interface creation section determines the position of center of gravity of the newly created first conforming granule cluster area and the position of center of gravity of the newly created first nonconforming granule cluster area, and sets an interface calculated based on the Euclidean distance at which the positions of center of gravity lie at the largest distance from each other all over the three-dimensional color distribution to partition the data into the two areas including the second conforming granule cluster area mostly containing conforming granules and the second nonconforming granule cluster area mostly containing nonconforming granules and foreign substances, dividing the data into approximately two clusters different from the above-described clusters. Then, the threshold determination section determines the line of intersection between the interface for the Mahalanobis distance and the interface for the Euclidean distance to set the line of intersection itself to a threshold that allows determination of whether or not the granules are to be treated as a separation target. That is, the granule sample plotted on the three-dimensional color space is generally separated into the first conforming granule cluster area and the first nonconforming granule cluster area based on the Mahalanobis distance interface. Then, an interface with a wide effective range of sensitivity is searched for based on the Euclidean distance interface, and the granule sample is separated into the second conforming granule cluster area and the second nonconforming granule cluster area. Moreover, upon determining the line of intersection itself between the interface for the Mahalanobis distance and the interface for the Euclidean distance to be the threshold, the threshold determination section can calculate a threshold on a two-dimensional color space. Thus, an optical type granule sorting machine can be provided which allows an operator to easily perform sensitivity setting by effectively utilizing RGB three-dimensional color space information similar to information acquired via human eyes and which also allows signal processing to be substantially simplified.

According to Claim 2, the present invention takes technical measures by providing an optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on individual color information on the granules inspected by the inspection means, and exclusion means for excluding the separation target determined by the determination means from the continuous flow, wherein the inspection means includes an illumination section that illuminates the granules with light and an optical detection section that detects light transmitted through the granules or reflected from the granules, and the determination means includes a three-dimensional color distribution data creation section that plots wavelength components of R light, G light, and B light from the granules detected by the optical detection section on a three-dimensional color space to create three-dimensional color distribution data for a granule sample, a learning and storing section that allows samples for conforming granules, nonconforming granules, and foreign substances preliminarily prepared by an operator to flow to the transfer means so that, when the optical detection section detects each of the samples to create three-dimensional color distribution data and the sample is displayed on an image, the operator visually classifies the sample as conforming granules, nonconforming granules, or foreign substances and the learning and storing section performs learning in association with the three-dimensional color distribution data, a Mahalanobis distance interface creation section that sets an interface calculated based on a Mahalanobis distance in the three-dimensional color distribution data created by the learning and storing section to partition the data into a first conforming granule cluster area containing many conforming granules and a first nonconforming granule cluster area containing many nonconforming granules and foreign substances, a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area containing many conforming granules and a second nonconforming granule cluster area containing many nonconforming granules and foreign substances, a threshold determination section that determines a line of intersection between the interface calculated based on the Mahalanobis distance and the interface calculated based on the Euclidean distance, to determine the line of intersection to be a determination threshold that allows determination of whether or not the granules are to be treated as a separation target, and a conforming granule/nonconforming granule determination section that considers the granules to be a separation target if the data created on the three-dimensional color distribution data is determined not to belong to the threshold determined by the threshold determination section when a material is allowed to flow to the transfer means and a sorting operation is performed.

Thus, even if the granules include conforming granules that are similar in color to nonconforming granules (for example, for brown rice, milky white grains as nonconforming granules are similar in color to regular brown rice as conforming granules, and rusty rice as nonconforming granules are similar in color to regular brown rice as conforming granules), the conforming granules are reliably sorted from the nonconforming granules to allow high-performance sorting to be implemented because the optical type granule sorting machine enables the operator to visually learn and associate the three-dimensional color distribution data with the sample displayed on the image instead of making ambiguous improvements on image processing. Thus, the optical type granule sorting machine is very practical.

DESCRIPTION OF EMBODIMENTS

Figure 1:
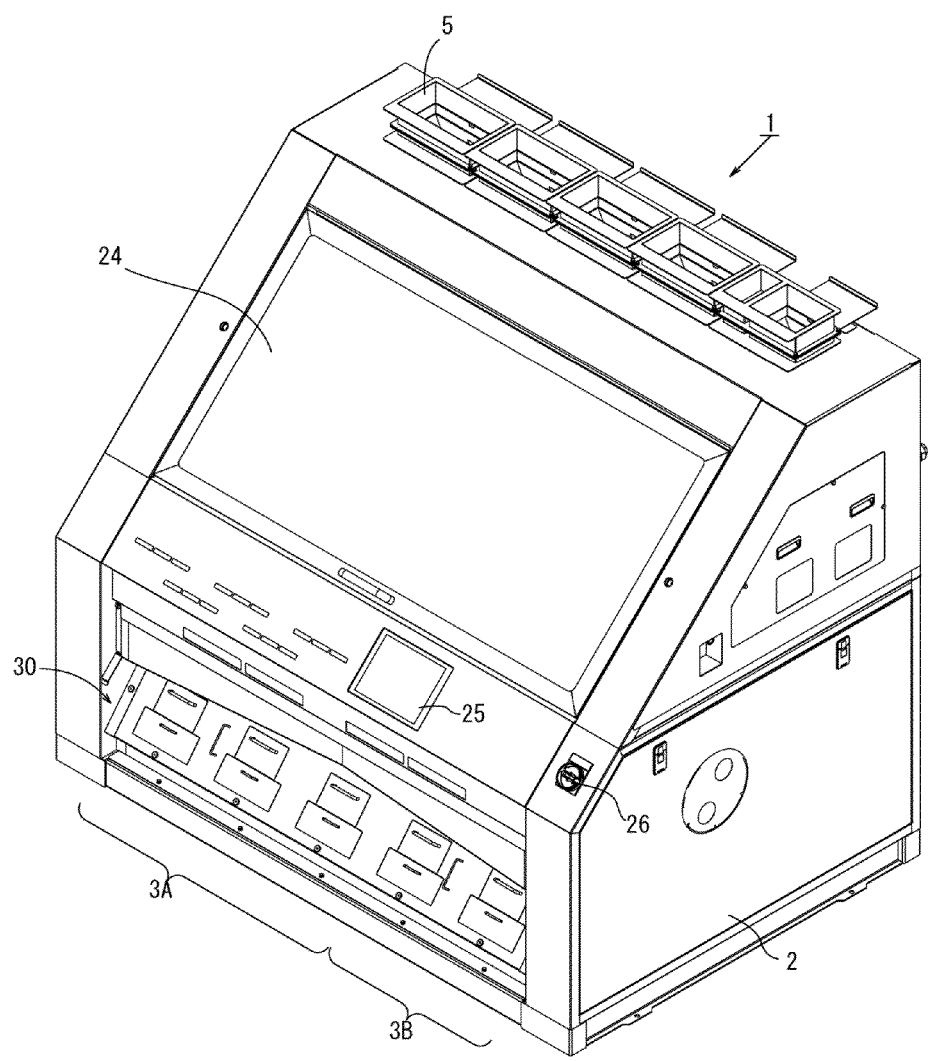
FIG. 1 is a perspective view depicting a whole optical type granule sorting machine.
Figure 2:
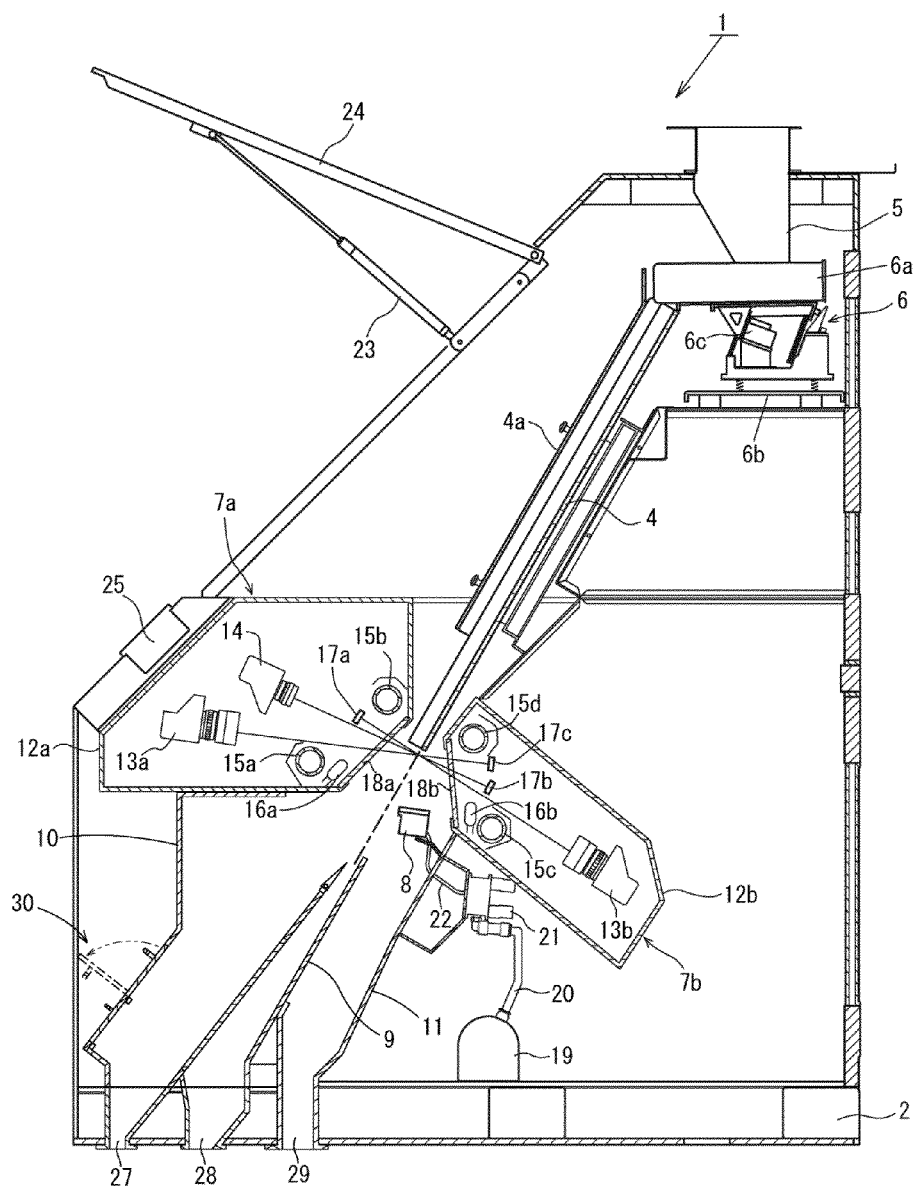
FIG. 2 is a schematic vertical cross-sectional view depicting the internal structure of the sorting machine.
Figure 3:
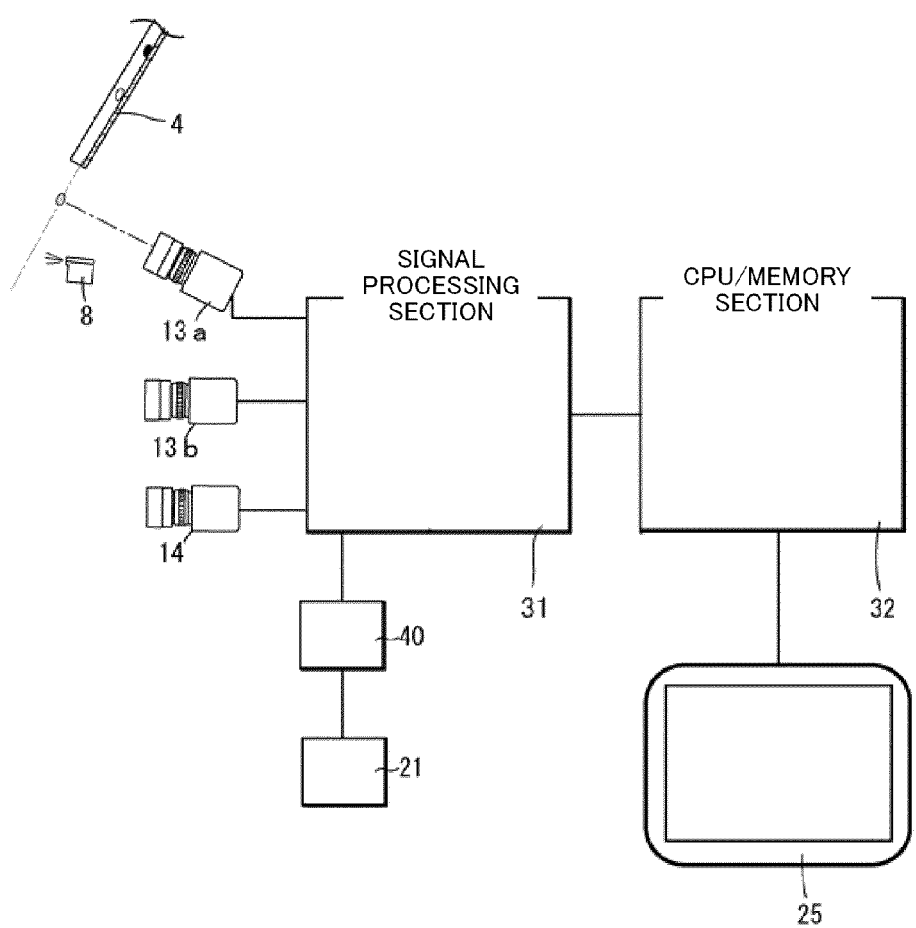
FIG. 3 is a block diagram of signal processing means for processing signals obtained from a camera in the sorting machine.
Figure 4:
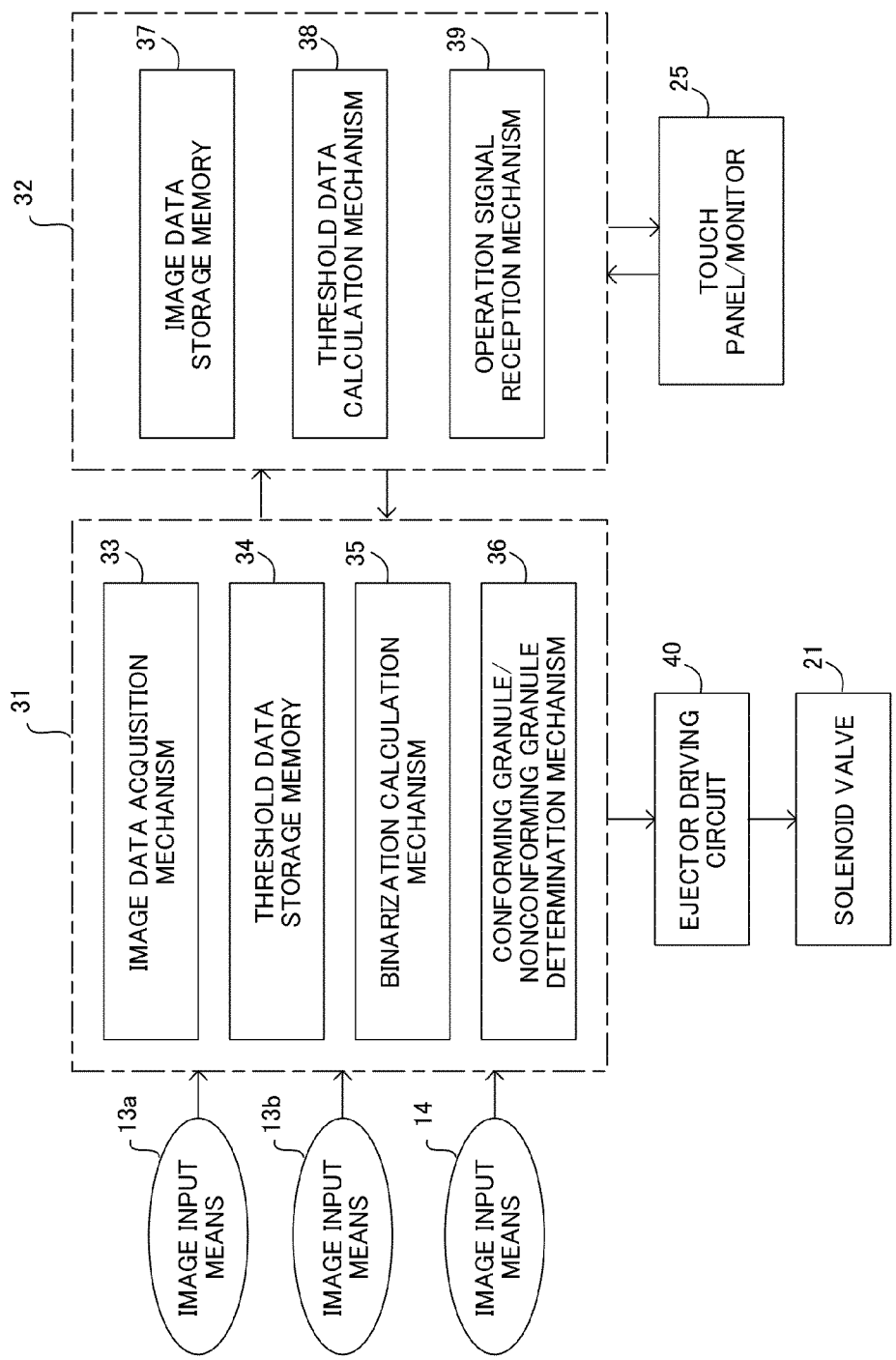
FIG. 4 is a block diagram conceptually illustrating a signal processing section and a CPU and a memory all depicted in FIG. 3.

An embodiment of the present invention will be described with reference to the drawings. FIG. 1 is a perspective view depicting the whole optical type granule sorting machine according to the present invention. FIG. 2 is a schematic vertical cross-sectional view depicting the internal structure of the sorting machine. FIG. 3 is a block diagram of signal processing means for processing signals obtained from a camera in the sorting machine. FIG. 4 is a conceptual diagram illustrating the internal structure of a signal processing section and a CPU and a memory all depicted in FIG. 3.

As depicted in FIG. 1, an optical type granule sorting machine 1 includes a generally trapezoidal machine frame 2 in which a plurality of primary sorting sections 3A (up to the third sorting section from the left end of FIG. 1) and a plurality of secondary sorting sections 3B (up to the second sorting section from the right end of FIG. 1) are arranged in juxtaposition. Each of the sorting sections 3A and 3B includes components arranged therein which are similar to corresponding components according to the conventional technique. In the present embodiment, the plurality of primary sorting sections 3A and the plurality of secondary sections 3B are arranged in juxtaposition. However, the present invention is not limited to this, and many variations may be set, such as a configuration in which a plurality of primary sorting sections, a single secondary sorting section, and a single tertiary sorting section are arranged in juxtaposition.

Now, components of the primary sorting section 3A will be described with reference to FIG. 2. The primary sorting section 3A includes a chute 4 arranged so as to incline at an angle of about 60 degrees to a horizontal position and serving as transfer means, a storage tank 5 in which granules such as grains are stored, a vibrating feeder 6 that conveys the granules from the storage tank 5 to the chute 4, optical detection sections 7 (7a and 7b) provided above and below, respectively, a falling trajectory of the granules falling from a lower end of the chute 4, an ejector nozzle 8 provided below the optical detection sections 7, a conforming granule collection gutter 9 located below the ejector nozzle 8 on the same inclined line as that of the chute 4 to receive the granules falling along the falling trajectory without receiving air blown through the ejector nozzle 8, a nonconforming granule collection gutter 10 juxtaposed with the conforming granule collection gutter 9 to receive air blown through the ejector nozzle 8 to collect nonconforming granules from the normal granules, and an auxiliary nonconforming granule collection gutter 11 that collects nonconforming granules impinging against and bouncing back from peripheral members after failing to receive air blown from the ejector nozzle 8.

In the primary sorting section 3A, the chute 4 is preferably shaped like a flat plate with no groove portion so as to allow granules to slide over a wide zone. A chute cover 4a may be provided at a predetermined distance from a bottom surface of the chute 4 in order to prevent granules from overflowing from the chute 4 and to prevent sorting target granules from floating from the bottom surface during sliding in the chute 4.

The vibrating feeder 6 includes a feeder trough 6a supported on a support section 6b and is configured to be able to feed granules to the chute 4 when a vibration apparatus such as a solenoid coil 6c is actuated.

The optical detection sections 7a and 7b are formed by being enclosed by boxes 12a and 12b, respectively. The box 12a located above the falling trajectory of the grain contains a CCD camera 13a for visible light, an NIR camera 14 for near infrared light, visible light sources 15a and 15b each including a fluorescent lamp, a near infrared light source 16a including a halogen lamp, and a background 17a opposite to the optical detection section 7b. On the other hand, the box 12b located below the falling trajectory of the grain contains a CCD camera 13b for visible light, visible light sources 15c and 15d each including a fluorescent lamp, a near infrared light source 16b including a halogen lamp, and background 17b and 17c opposite to the optical detection section 7a. The boxes 12a and 12b include window members 18a and 18b, respectively, fitted therein on the falling trajectory side of the grain and including transparent glass.

The ejector nozzle 8 is fed with air from an air compressor not depicted in the drawings, through a tube 22 via a subtank 19, an air pipe 20, and a solenoid valve 21. The subtank 19 temporarily stores air from the air compressor. The provision of the subtank 19 prevents shortage of air even if a large amount of air is consumed from the ejector nozzle 8.

An inclined wall in a front portion of the machine frame 2 is provided with a front door 24 that can be rotationally moved in an up-down direction by the air cylinder 23. This enables maintenance work such as cleaning to be facilitated. On the other hand, below the front door 24, a control panel including a touch panel, a liquid crystal display 25 also serving as a monitor, and a power supply switch 26 are provided. Thus, when the liquid crystal display 25 and the power supply switch 26 are disposed at the height position of an operator's eyes, machine operations can be easily performed.

Now, a configuration of the secondary sorting section 3B will be described. A difference between the secondary sorting section 3B and the primary sorting section 3A is the shape of the chute 4; the chute 4 for the secondary sorting section 3B includes a plurality of groove portions formed therein to allow grains to slide so as to be divided into a plurality of columns. An appropriate cross-sectional shape may be adopted for the groove portion; the cross section may be, for example, U- or V-shaped or recessed. The remaining part of configuration of the secondary sorting section 3B is approximately similar to the corresponding part of configuration of the primary sorting section 3A. Reference numeral 27 in FIG.

2 denotes a nonconforming granule faucet. Reference numeral 28 in FIG. 2 denotes a conforming granule faucet. Reference numeral 29 denotes an auxiliary nonconforming granule faucet. Reference numeral 30 denotes a sample slot.

A configuration of signal processing means will be described with reference to FIGS. 3 and 4. The CCD cameras 13a and 13b for visible light and the NIR camera 14 are electrically connected to a signal processing section 31 in order to allow a binarization process to be executed on images taken by the cameras and also to a CPU and memory section 32 that stores the binarized images from the signal processing section 31 and applies a needed process to the images. The liquid crystal display 25 is electrically connected to the CPU and memory section 32.

Referring to FIG. 4, the signal processing section 31 includes an image data acquisition mechanism 33 that temporarily stores image data, a threshold data storage memory 34 that stores threshold data allowing determination of whether acquired image data indicates conforming granules or nonconforming granules, a binarization calculation mechanism 35 that executes a binarization process on the acquired image data, and a conforming granule/nonconforming granule determination mechanism 36 that determines whether the acquired image data indicates conforming granules or nonconforming granules. On the other hand, the CPU and memory section 32 includes an image data storage memory 37 that stores the data from the image data acquisition mechanism 33 as needed, a threshold data calculation mechanism 38 that calculates the threshold in order to execute a process that is an important part of the present invention based on the image data stored in the image data storage memory 37, and an operation signal reception mechanism 39 that receives a signal for a touch operation on the liquid crystal display 25 and outputs the processed image data to the monitor.

The conforming granule/nonconforming granule determination mechanism 36 in the signal processing section 31 is electrically connected to an ejector driving circuit 40 to which a solenoid valve 21 allowing air to be blown through the ejector nozzle 8 based on a signal from the driving circuit 40 is electrically connected.

The effects of the optical type granule sorting machine configured as described above will be described in detail.

Figure 5:
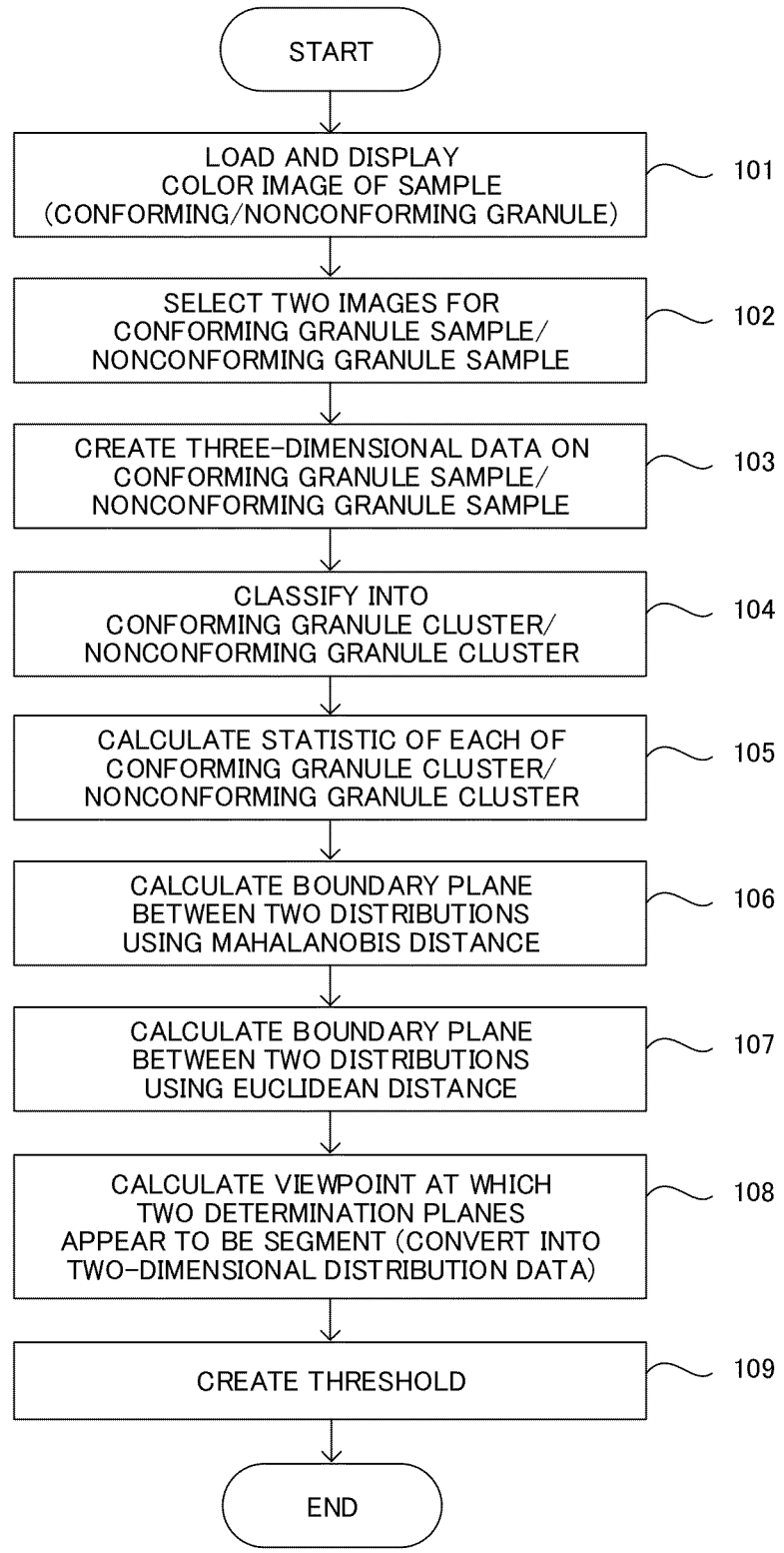
FIG. 5 is a flow diagram depicting an operating procedure executed by the signal processing section.

FIG. 5 is a flowchart depicting an operating procedure for the signal processing section. In FIG. 5, steps 101 to 103 correspond to conforming granule pattern/nonconforming granule pattern learning steps in which, after samples for a conforming granule, a nonconforming granule, and a foreign substance preliminarily prepared by an operator are allowed to flow through the chute, the sorting machine is allowed to learn three-dimensional color distribution patterns for the conforming granule, the nonconforming granule, and the foreign substance. Steps 104 to 108 correspond to threshold calculation steps of automatically calculating a threshold serving as a boundary between the conforming granule pattern and the nonconforming granule pattern. Step 109 is a threshold determination step in which the operator fine-tunes the threshold calculated in the threshold calculation steps.

(Conforming Granule Pattern/Nonconforming Granule Pattern Learning Steps)

The pattern learning steps are a preparatory operation before sorting, and thus, the ejector nozzle 8 is not actuated. When the operation is started, first in step 101, a conforming granule sample prepared by a skilled operator by means of sorting is allowed to flow from the storage tank 5 onto the chute 4. Images of the conforming granule sample falling from a lower end of the chute 4 are picked up by the CCD cameras 13a and 13b and the NIR camera 14. Then, a large number of image data on the conforming granule sample taken by the CCD cameras 13a and 13b and the NIR camera 14 are input to the image data storage memory 37 via the image data acquisition mechanism 33. The images are displayed on the monitor of the liquid crystal display 25. When the acquisition of the image data on the conforming granule sample ends, then an operation similar to the above-described operation is performed on a nonconforming granule sample (including a foreign substance sample) prepared by the skilled operator by means of sorting to acquire image data on the nonconforming granule sample (including a foreign substance sample).

Then, the process proceeds to step 102. For the samples displayed on the liquid crystal display 25, the operator visually specifies, on the images, a sample to be considered to be a conforming granule, a sample to be considered to be a nonconforming granule, and a sample to be considered to be a foreign substance again. Then, the process proceeds to step 103. The specified conforming granule sample image is considered to be one area, and the nonconforming granule sample image is also considered to be one area. A large number of such images are plotted on a three-dimensional color space (in the embodiment, a color space with an R axis, a G axis, and a B axis). Thus, an aggregate is sequentially formed on the RGB color space as depicted in FIG. 6.

(Threshold Calculation Step)

Figure 6:
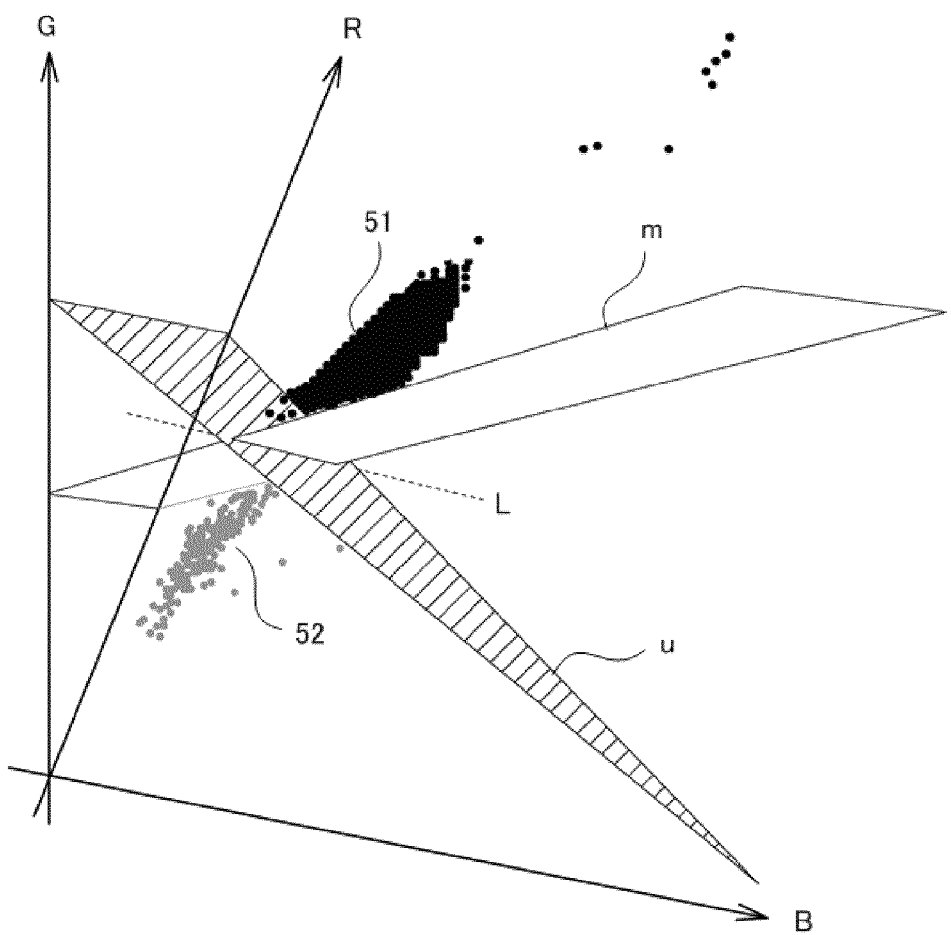
FIG. 6 is an RGB correlation diagram of a conforming granule sample and a nonconforming granule sample on a three-dimensional color space.

In step 104, the data are roughly classified into a conforming granule cluster 51 (aggregate) formed of dots for conforming granules (black points in FIG. 6) and nonconforming granule cluster 52 (aggregate) formed of dots for nonconforming granules (gray points in FIG. 6) (see FIG. 6). In step 105, the statistic of multivariate data is calculated for each of the conforming granule cluster 51 and the nonconforming granule cluster 52.

The calculation of the statistics may be performed by calculating center-of-gravity vectors or variance/covariance matrices. For example, an arithmetic expression for a center-of-gravity vector is as follows:

[Formula 1]

$$\overline{X} = (\overline{X_1}, \overline{X_2}, \ldots, \overline{X_n}) \quad (1)$$
$$\overline{X_i} = \frac{1}{S}\sigma_{k=1}^{S} X_{ik}$$

S: the number of samples.

Furthermore, an arithmetic expression for a variance/covariance matrix is as follows.

[Formula 2]

$$C_{ij} = \frac{1}{S}\sigma_{k=1}^{S}(X_{ik} - \overline{X_i})(X_{jk} - \overline{X_j}) \quad (2)$$

Then, a Mahalanobis square distance from the center-of-gravity vector for each of the conforming granule/nonconforming granule clusters is determined. Here, the Mahalanobis square distance is a function of the value of multivariate data. An arithmetic expression for the Mahalanobis square distance is as follows.

[Formula 3]

$$D_m^2 = (\alpha - \overline{\alpha_m})^t A^{-1}(\alpha - \overline{\alpha_m}) \quad (3)$$

where
   m: an index for the cluster,
   A: a variance/covariance matrix, and
   $\alpha_m$: a center-of-gravity vector for the cluster m.

Then, an interface between the clusters is determined (step 106). When the interface is determined, the values of multivariate data are classified into clusters with the minimum Mahalanobis square distance. For the values of all multivariate data in the multivariate space, the cluster to which the value belongs is determined. Then, the interface depicted by reference character m in FIG. 6 is determined.

Then, a Euclidean distance is selected which involves the longest center-of-gravity distance between a conforming granule cluster 51 and a nonconforming granule cluster 52, and an interface with a wide effective range of sensitivity is searched for (step 107). In this regard, when the center-of-gravity vector for the conforming granule cluster is denoted by P(Xp1, Xp2, Xp3, . . . , Xpn) and the center-of-gravity vector for the nonconforming granule cluster is denoted by Q(Xq1, Xq2, Xq3, . . . , Xqn), the Euclidean square distance between the centers of gravity is expressed by:
[Formula 4]

$$d^2 = \sigma_{i=1}^{n}(X_{p1}-X_{q1})^2 \tag{4}$$

Then, the interface between the clusters is determined (step 107). When the interface is determined, the values of the multivariate data are classified into clusters with the maximum Euclidean square distance, and the interface depicted by reference character u in FIG. 6 is determined.

Then, it is assumed that an equation for the plane m of the interface that minimizes the Mahalanobis distance is expressed by Formula (5), whereas an equation for the plane u of the interface that maximizes the Euclidean distance is expressed by Formula (6).
[Formula 5]

$$m: a_1 x + b_1 y + c_1 z = d_1 \tag{5}$$

[Formula 6]

$$u: a_2 x + b_2 y + c_2 z = d_1 \tag{6}$$

The two characteristic planes m and u as depicted in FIG. 6 are obtained. Then, the correlation diagram in FIG. 6 is turned such that a viewing direction (viewing vector) aligns with a position where the two different planes m and u intersect each other and appear to be a segment (step 108 in FIG. 5). Thus, the optimum threshold with the number of dimensions in the color space reduced from three to two is determined. This allows provision of an optical type granule sorting machine which allows signal processing to be substantially simplified and which can be easily used by the operator.

A segment L (see FIG. 6) resulting from the intersection of the plane m expressed by Formula (5) and the plane u expressed by Formula (6) can be determined as follows.
[Formula 7]

$$P = A + te \tag{7}$$

where
   A: a point passing through a line of intersection L,
   e: a directional vector for the line of intersection, and
   t: a parameter.

Then, when the direction vector e for the line of intersection is determined by executing an exterior substance calculation on normal vectors for the two planes m and u, Formula (8) holds true.
[Formula 8]

$$e = [b1c2-c1b2 \; c1a2-a1c2 \; a1b2-b1a2] \tag{8}$$

Here, the following are assumed: Xe=b1c2−c1b2, Ye=c1a2−a1c2, and Ze=a1b2−b1a2.

The point P through which the line of intersection L passes is expressed as follows.
[Formula 9]

For $Ze \neq 0$, ((d1b2−d2b1)/Ze,(d1a2−d2a1)/(−Ze),0),

For $Ye \neq 0$, ((d1c2−d2c1)/(−Ye),0,(d1a2−d2a1)/Ye),

For $Xe \neq 0$, (0,((d1c2−d2c1)/Xe,(d1b2−d2b1)/(−Xe)), and

For $Xe=0$, $Ye=0$, and $Ze=0$, no line of intersection is formed (the two planes are parallel to each other) (9)

Figure 7:
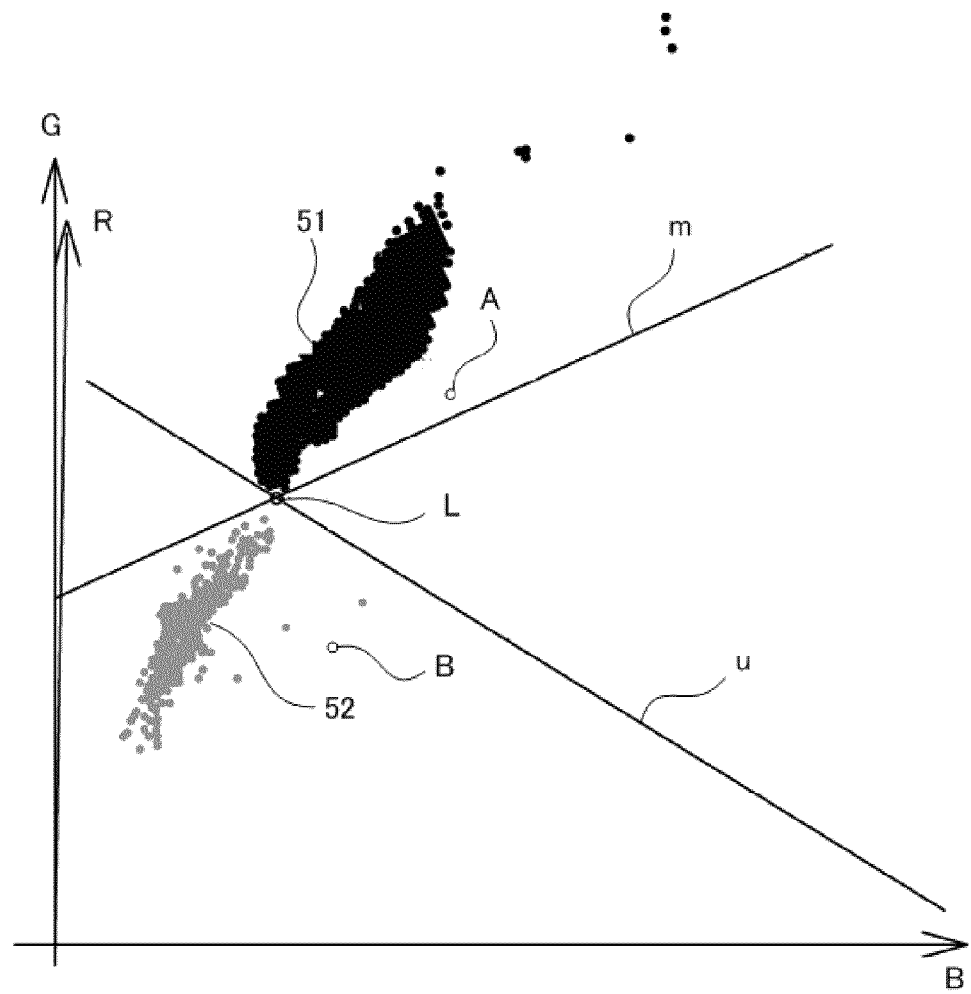
FIG. 7 is an RGB correlation diagram of a conforming granule sample and a nonconforming granule sample on an optimum two-dimensional display surface.

When the line of intersection L is determined as described above, a conversion into an RGB correlation diagram for an optimum two-dimensional display surface with a viewpoint placed on the line of intersection L is enabled (see FIG. 7).
(Threshold Determination Step)

As described above, the operator determines a determination threshold for conforming granules and nonconforming granules based on the line of intersection L on the two-dimensional space in FIG. 7 (step 109 in FIG. 5). This enables the determination of the optimum threshold with the number of dimensions in the color space reduced from three in FIG. 6 to two in FIG. 7. Thus, an optical type granule sorting machine can be provided which enables signal processing to be substantially simplified and which allows the operator to easily set the optimum threshold and which can be easily used by the operator. The threshold setting operation before the actual operation of the optical type granule sorting machine has been described.
(Sorting Operation)

After the above-described threshold setting operation, the following are performed: specification of a material (grain or granule, the type of the grain, and the like), adjustment of flow rate (setting of a target flow rate), adjustment of sensitivity of sorting substances (whether or not foreign substances (glass and stones) and colored granules (nonconforming granule, milky rice, slightly altered rice, and the like) are sorted or removed from sorting targets), adjustment of delay time in the ejector, and the like. Subsequently, a material is supplied to the storage tank 5, and a sorting switch on the control panel including a touch panel is selected. Thus, a program that starts a sorting operation is initiated, and the threshold is loaded from the threshold storage memory 34 in FIG. 4, the threshold being set as described above to allow determination of whether the granules are conforming or nonconforming. Then, the CPU and memory section 32 determines whether the granules are conforming or nonconforming based on the threshold.

In this state, when the vibrating feeder 6 is started, the material supplied to the storage tank 5 is fed onto the chute 4. The material falls from the lower end of the chute 4 and is detected by the optical detectors 7a and 7b.

In this regard, images of the material flowing down between the optical detectors 7a and 7b are picked up by the CCD cameras 13a and 13b and the NIR camera 14. The image pickup data are temporarily stored in the image data storage memory 37 via the image data acquisition mechanism 33. Then, as described in the conforming granule pattern/nonconforming granule pattern learning steps and the threshold calculation steps, the data on the material are plotted on the three-dimensional color space and then converted onto the two-dimensional color space. That is, the granule to be sorted and determined is a granule A or a granule B in FIG. 7.

On the other hand, the current threshold stored in the threshold data storage memory 34 can be schematically depicted as the line of intersection L in FIG. 7. On FIG. 7, the line of intersection L serves as a boundary line. An area above the boundary line L depicts a conforming granule area, whereas an area below the boundary line L depicts a nonconforming granule area.

As depicted in FIG. 7, if the granule A is within the conforming granule area above the boundary line L, the conforming granule/nonconforming granule determination mechanism 36 in FIG. 4 determines that the "granule A is a conforming granule". The ejector driving circuit 41 issues no removal signal, and the granule A is collected in the conforming granule faucet 9 as a conforming granule (see FIG. 2). On the other hand, if the granule B is within the nonconforming granule area below the boundary line L, the conforming granule/nonconforming granule determination mechanism 36 in FIG. 4 determines that the "granule B is a nonconforming granule". Thus, the ejector driving circuit 41 issues a removal signal to the solenoid valve 21. The granule B is removed from the material flowing downward, by high-pressure air blown through the ejector nozzle 8. The granule B is then collected in the nonconforming granule faucet 27 as a nonconforming granule (see FIG. 2).

The opposite setting may be made by considering the conforming granule cluster in FIG. 6 and FIG. 7 to be a nonconforming granule cluster, while considering the nonconforming granule cluster in FIG. 6 and FIG. 7 to be a conforming granule cluster. Normally, the nonconforming granules account for a very low percentage of the material compared to the conforming granules and can thus be sorted and removed by blowing high-pressure air from the ejector nozzle 8 against the nonconforming granules. However, if the conforming granules accounts for a very low percentage of the material compared to the nonconforming granules, sorting efficiency is increased by considering the conforming granules to be nonconforming granules and blowing high-pressure air from the ejector nozzle 8 against the conforming granules to sort and remove the conforming granules. This is referred to as "reverse out", and a relevant control mechanism is conventionally incorporated into a color sorting machine. The operator can make appropriate settings taking into account, for example, the rate of nonconforming granules mixed in the material granules. Simply rewriting the data in the threshold data storage memory 34 allows setting of an operation of considering the conforming granule cluster in FIG. 6 and FIG. 7 to be a nonconforming granule cluster, while considering the nonconforming granule cluster in FIG. 6 and FIG. 7 to be a conforming granule cluster. When the operator sets "reverse out", the conforming granules are subjected to high-pressure air from the ejector nozzle 8 and collected in the nonconforming granule faucet 27. On the other hand, the nonconforming granules are collected in the conforming granule faucet 9 without being subjected to high-pressure air from the ejected nozzle 8.

As described above, according to the present invention, the determination section that determines whether or not the granules are to be treated as a separation target based on the individual color information on the granules includes the three-dimensional color distribution data creation section, the Mahalanobis distance interface creation section, the Euclidean distance interface creation section, and the threshold determination section. Thus, the three-dimensional color distribution data creation section plots the wavelength components of R light, G light, and B light from the granules on the three-dimensional color space to create the entire three-dimensional color distribution for a granule sample. Then, the Mahalanobis distance interface creation section sets an interface calculated based on the Mahalanobis distance, and divides the data into approximately two clusters, the conforming granule cluster area and the nonconforming granule cluster area. Moreover, the Euclidean distance interface creation section determines the position of the center of gravity of the conforming granule cluster area and the position of the center of gravity of the nonconforming granule cluster area, and sets, all over the three-dimensional color distribution, an interface calculated based on the Euclidean distance and involving the longest distance between the positions of the center of gravity. The threshold determination section determines the line of intersection between the interface for the Mahalanobis distance and the interface for the Euclidean distance, and sets the line of intersection to be a threshold allowing determination of whether or not the granules are to be treated as a separation target. Thus, the granule sample plotted on the three-dimensional color space can be roughly separated into a conforming granule cluster area and a nonconforming granule cluster area by the Mahalanobis distance interface. Then, an interface with a wide effective range of sensitivity can be searched for based on the Euclidean distance interface. Moreover, the threshold determination section can calculate a threshold on the two-dimensional color space. Therefore, an optical type granule sorting machine can be provided which allows a sensitivity setting to be easily performed by effectively utilizing RGB three-dimensional color space information similar to information obtained via human eyes and which enables signal processing to be substantially simplified.

The color sorting machine according to the present invention is not limited to the above-described embodiment. Various changes may be made to the design of the embodiment. For example, the chute is adopted as the transfer means, but may be configured to include a plurality of stages such as two vertical stages or three vertical stages. Alternatively, a belt conveyor or the like may be used as the transfer means. Furthermore, the high-speed air ejector nozzle that blows high-pressure air is adopted as the exclusion means for excluding the separation target from the continuous flow. However, instead of the high-speed ejector nozzle, a push ejector means such as an air cylinder may be used which excludes the separation target from the continuous flow.

As described above, the present invention is evidently a novel and useful optical type granule sorting machine which allows sensitivity setting to be easily performed by effectively utilizing RGB three-dimensional color space information similar to information obtained via human eyes and which enables signal processing to be substantially simplified.

INDUSTRIAL APPLICABILITY

The present invention is applicable to an optical type granule sorting machine that sorts a material including grains such as rice, wheat, beans, or nuts, resin pieces such as pellets or beads, medicines, ores, fine articles such as white baits, or other granules into conforming granules and nonconforming granules and excludes foreign substances or the like mixed in the material.

REFERENCE SIGNS LIST

1 Optical type granule sorting machine
2 Machine frame
3A Primary sorting section
3B Secondary sorting section
4 Chute 5 Storage tank
6 Vibrating feeder
7 Optical detection section
8 Ejector nozzle
9 Conforming granule collection gutter
10 Nonconforming granule collection gutter
11 Auxiliary nonconforming granule collection gutter
12 Box
13 CCD camera
14 NIR camera
15 Visible light source
16 Near infrared light source
17 Background
18 Window member
19 Subtank
20 Air pipe
21 Solenoid valve
22 Tube
23 Air cylinder
24 Front door
25 Liquid crystal display
26 Power supply switch
27 Nonconforming granule faucet
28 Conforming granule faucet
29 Auxiliary nonconforming granule faucet
30 Sample slot
31 Signal processing section
32 CPU and memory section
33 Image data acquisition mechanism
34 Threshold data storage memory
35 Binarization calculation mechanism
36 Conforming granule/nonconforming granule determination mechanism
37 Image data storage memory
38 Threshold data calculation mechanism
39 Operation signal reception mechanism
40 Ejector driving circuit
51 Conforming granule cluster
52 Nonconforming granule cluster

The invention claimed is:

1. An optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on individual color information on the granules inspected by the inspection means, and exclusion means for excluding the separation target determined by the determination means from the continuous flow, wherein the inspection means includes an illumination section that illuminates the granules with light and an optical detection section that detects light transmitted through the granules or reflected from the granules, and the determination means includes a three-dimensional color distribution data creation section that plots wavelength components of R light, G light, and B light from the granules detected by the optical detection section on a three-dimensional color space to create three-dimensional color distribution data for a granule sample;

a Mahalanobis distance interface creation section that sets an interface calculated based on a Mahalanobis distance in the three-dimensional color distribution data created by the three-dimensional distribution data creation section to partition the data into a first conforming granule cluster area containing many conforming granules and a first nonconforming granule cluster area containing many nonconforming granules and foreign substances;

a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area and a second nonconforming granule cluster area; and a threshold determination section that determines a line of intersection between the interface calculated based on the Mahalanobis distance and the interface calculated based on the Euclidean distance, to determine the line of intersection to be a determination threshold that allows determination of whether or not the granules are to be treated as a separation target.

2. An optical type granule sorting machine comprising transfer means for transferring granules including conforming granules, nonconforming granules, and foreign substances in such a manner that the granules form a continuous flow, inspection means for inspecting the granules transferred by the transfer means, determination means for determining whether or not the granules are to be treated as a separation target based on individual color information on the granules inspected by the inspection means, and exclusion means for excluding the separation target determined by the determination means from the continuous flow, wherein the inspection means includes an illumination section that illuminates the granules with light and an optical detection section that detects light transmitted through the granules or reflected from the granules, and the determination means includes a three-dimensional color distribution data creation section that plots wavelength components of R light, G light, and B light from the granules detected by the optical detection section on a three-dimensional color space to create three-dimensional color distribution data for a granule sample;

a learning and storing section that allows samples for conforming granules, nonconforming granules, and foreign substances preliminarily prepared by an operator to flow to the transfer means so that, when the optical detection section detects each of the samples to create three-dimensional color distribution data and the sample is displayed on an image, the operator visually classifies the sample as conforming granules, nonconforming granules, or foreign substances and the learning and storing section performs learning in association with the three-dimensional color distribution data;

a Mahalanobis distance interface creation section that sets an interface calculated based on a Mahalanobis distance in the three-dimensional color distribution data created by the learning and storing section to partition the data into a first conforming granule cluster area containing many conforming granules and a first nonconforming granule cluster area containing many nonconforming granules and foreign substances;

a Euclidean distance interface creation section that determines a position of center of gravity of the first conforming granule cluster area created by the Mahalanobis distance interface creation section and a position of center of gravity of the first nonconforming granule cluster area created by the Mahalanobis distance interface creation section, the Euclidean distance interface creation section setting an interface calculated based on a Euclidean distance at which the positions of center of gravity lie at a longest distance from each other to partition the data into a second conforming granule cluster area containing many conforming granules and a second nonconforming granule cluster area containing many nonconforming granules and foreign substances;

a threshold determination section that determines a line of intersection between the interface calculated based on the Mahalanobis distance and the interface calculated based on the Euclidean distance, to determine the line of intersection to be a determination threshold that allows determination of whether or not the granules are to be treated as a separation target; and a conforming granule/nonconforming granule determination section that considers the granules to be a separation target if the data created on the three-dimensional color distribution data is determined not to belong to the threshold determined by the threshold determination section when a material is allowed to flow to the transfer means and a sorting operation is performed.

\* \* \* \* \*